United States Patent
Snow et al.

(10) Patent No.: US 12,196,754 B2
(45) Date of Patent: Jan. 14, 2025

(54) METHOD AND SYSTEM FOR BUOYANT-PARTICLE-ASSISTED CELL THERAPY

(71) Applicant: Akadeum Life Sciences, Inc., Ann Arbor, MI (US)

(72) Inventors: Tiffany Snow, Ann Arbor, MI (US); Jonathan Roussey, Ann Arbor, MI (US); Casey Wegner, Ann Arbor, MI (US); Brandon H. McNaughton, Ann Arbor, MI (US)

(73) Assignee: Akadeum Life Sciences, Inc., Ann Arbor, MI (US)

( * ) Notice: Subject to any disclaimer, the term of this patent is extended or adjusted under 35 U.S.C. 154(b) by 0 days.

(21) Appl. No.: 18/114,130

(22) Filed: Feb. 24, 2023

(65) Prior Publication Data

US 2023/0314428 A1    Oct. 5, 2023

Related U.S. Application Data

(60) Provisional application No. 63/434,363, filed on Dec. 21, 2022, provisional application No. 63/326,446, filed on Apr. 1, 2022.

(51) Int. Cl.
*G01N 33/569* (2006.01)
*B01D 21/00* (2006.01)
*G01N 33/543* (2006.01)

(52) U.S. Cl.
CPC ............... *G01N 33/56972* (2013.01); *B01D 21/0084* (2013.01); *G01N 33/5432* (2013.01)

(58) Field of Classification Search
CPC ............... G01N 33/56972; G01N 33/5432
See application file for complete search history.

(56) References Cited

U.S. PATENT DOCUMENTS

| 3,381,283 A | 4/1968 | Gyorgy et al. |
| 3,586,064 A | 6/1971 | Brown et al. |
| 3,692,493 A | 9/1972 | Terasaki |

(Continued)

FOREIGN PATENT DOCUMENTS

| DE | 3381283 | 4/1990 |
| EP | 0778944 B1 | 11/1999 |

(Continued)

OTHER PUBLICATIONS

Corrosionpedia—Diaphragm Pump—Published: Oct. 2, 2014 Updated: May 4, 2019 (Year: 2019).

(Continued)

*Primary Examiner* — Gailene Gabel
(74) *Attorney, Agent, or Firm* — Jeffrey Schox; Annie Imbrie-Moore

(57) ABSTRACT

A system for buoyant-particle-assisted cell therapy includes and/or interfaces with a set of buoyant particles. Additionally or alternatively, the system can include and/or interface with a processing container, a set of processing materials (e.g., buffers, factors, solutions, etc.), and/or any other components. A method for buoyant-particle-assisted cell therapy includes processing the set of cells of interest. Additionally or alternatively, the method can include any or all of: preparing a set of buoyant particles; receiving a sample; and isolating a set of cells of interest from the sample.

7 Claims, 9 Drawing Sheets

(56) References Cited

U.S. PATENT DOCUMENTS

| | | |
|---|---|---|
| 3,920,549 A | 11/1975 | Gigliello et al. |
| 4,086,060 A | 4/1978 | Hermann |
| 4,464,254 A | 8/1984 | Dojki et al. |
| 4,487,700 A | 12/1984 | Kanter |
| 4,689,151 A | 8/1987 | Kosikowski et al. |
| 4,714,680 A | 12/1987 | Civin |
| 4,845,025 A | 7/1989 | Lary et al. |
| 5,116,724 A | 5/1992 | Delaage et al. |
| 5,182,192 A | 1/1993 | Steplewski et al. |
| 5,246,829 A | 9/1993 | Delaage et al. |
| 5,266,199 A | 11/1993 | Tsukagoshi et al. |
| 5,339,830 A | 8/1994 | Blake |
| 5,354,483 A | 10/1994 | Furse |
| 5,594,164 A | 1/1997 | Bull |
| 5,639,382 A | 6/1997 | Brown |
| 5,674,173 A | 10/1997 | Hlavinka et al. |
| 5,730,864 A | 3/1998 | Delsalle et al. |
| 5,853,600 A | 12/1998 | McNeal et al. |
| 5,874,266 A | 2/1999 | Palsson |
| 6,036,940 A | 3/2000 | Ju et al. |
| 6,151,113 A | 11/2000 | ODonohue et al. |
| 6,221,315 B1 | 4/2001 | Giesler et al. |
| 6,261,537 B1 | 7/2001 | Klaveness et al. |
| 6,264,917 B1 | 7/2001 | Klaveness et al. |
| 6,331,289 B1 | 12/2001 | Klaveness et al. |
| 6,416,739 B1 | 7/2002 | Rogerson et al. |
| 6,506,167 B1 | 1/2003 | Ishimoto et al. |
| 6,528,039 B2 | 3/2003 | Unger |
| 6,544,424 B1 | 4/2003 | Shevitz |
| 6,569,340 B2 | 5/2003 | Kopf |
| 6,652,136 B2 | 11/2003 | Marziali |
| 6,723,303 B1 | 4/2004 | Quay |
| 6,919,031 B2 | 7/2005 | Blumenschein et al. |
| 7,524,641 B2 | 4/2009 | Jurgensen et al. |
| 7,704,393 B2 | 4/2010 | Noh et al. |
| 7,736,593 B2 | 6/2010 | Dastane et al. |
| 7,771,590 B2 | 8/2010 | Leach et al. |
| 7,915,540 B2 | 3/2011 | Oggioni |
| 7,947,236 B2 | 5/2011 | Losada et al. |
| 7,981,286 B2 | 7/2011 | Higuchi et al. |
| 8,048,320 B2 | 11/2011 | Leach et al. |
| 8,066,127 B2 | 11/2011 | Coelho et al. |
| 8,177,072 B2 | 5/2012 | Chapman et al. |
| 8,183,039 B2 | 5/2012 | Schmitz et al. |
| 8,290,714 B2 | 10/2012 | Ignatius et al. |
| 8,513,032 B2 | 8/2013 | Jablonski et al. |
| 8,540,082 B2 | 9/2013 | Kelland et al. |
| 8,617,884 B2 | 12/2013 | Berenson et al. |
| 8,747,289 B2 | 6/2014 | Coelho |
| 8,834,698 B2 | 9/2014 | Lau et al. |
| 8,835,186 B2 | 9/2014 | Jablonski et al. |
| 9,011,819 B2 | 4/2015 | Rychak |
| 9,039,999 B2 | 5/2015 | Campton et al. |
| 9,114,334 B2 | 8/2015 | Leach et al. |
| 9,119,508 B2 | 9/2015 | Reed |
| 9,120,095 B2 | 9/2015 | OConnell |
| 9,234,890 B2 | 1/2016 | Adams et al. |
| 9,410,182 B2 | 8/2016 | Wu |
| 9,410,183 B2 | 8/2016 | Wu |
| 9,435,799 B2 | 9/2016 | Russell et al. |
| 9,506,930 B2 | 11/2016 | Ignatius et al. |
| 9,528,088 B2 | 12/2016 | Berenson et al. |
| 9,551,706 B2 | 1/2017 | Phillips et al. |
| 9,599,545 B2 | 3/2017 | Coelho |
| 9,695,394 B1 | 7/2017 | Coelho et al. |
| 9,766,237 B2 | 9/2017 | Jablonski et al. |
| 9,790,467 B2 | 10/2017 | Kevlahan et al. |
| 9,797,817 B2 | 10/2017 | McNaughton et al. |
| 9,821,111 B2 | 11/2017 | Coelho et al. |
| 9,857,361 B2 | 1/2018 | Wanders et al. |
| 10,052,427 B2 | 8/2018 | Flieg et al. |
| 10,132,309 B2 | 11/2018 | Manzarek et al. |
| 10,195,280 B2 | 2/2019 | De Mollerat Du Jeu et al. |
| 10,195,547 B2 | 2/2019 | McNaughton et al. |
| 10,273,504 B2 | 4/2019 | Miltenyi et al. |
| 10,302,536 B2 | 5/2019 | Shi et al. |
| 10,407,486 B2 | 9/2019 | Schmitz et al. |
| 10,479,976 B2 | 11/2019 | Shi et al. |
| 10,585,088 B2 | 3/2020 | Gohel et al. |
| 10,640,275 B2 | 5/2020 | McGrath et al. |
| 10,640,276 B2 | 5/2020 | McGrath et al. |
| 10,684,172 B2 | 6/2020 | Carron et al. |
| 10,739,338 B2 | 8/2020 | Kevlahan et al. |
| 10,752,689 B2 | 8/2020 | Aggeler et al. |
| 10,792,362 B2 | 10/2020 | De Mollerat Du Jeu et al. |
| 10,794,900 B2 | 10/2020 | Wanders et al. |
| 10,859,477 B2 | 12/2020 | Nakamura et al. |
| 10,890,586 B2 | 1/2021 | Wu et al. |
| 10,934,519 B2 | 3/2021 | Roy et al. |
| 11,007,285 B2 | 5/2021 | Butts et al. |
| 11,046,738 B2 | 6/2021 | Person et al. |
| 11,105,796 B2 | 8/2021 | Fuerstenberg et al. |
| 11,141,435 B2 | 10/2021 | Coelho et al. |
| 11,155,714 B2 | 10/2021 | Xu et al. |
| 11,247,178 B2 | 2/2022 | Smyslova et al. |
| 11,291,931 B2 | 4/2022 | McNaughton et al. |
| 11,339,407 B2 | 5/2022 | Waters et al. |
| 11,524,985 B2 | 12/2022 | Kalabokis et al. |
| 11,565,237 B2 | 1/2023 | Kevlahan et al. |
| 11,819,842 B2 | 11/2023 | Wegner et al. |
| 2003/0066850 A1 | 4/2003 | Young |
| 2003/0104359 A1 | 6/2003 | Cuthbertson et al. |
| 2004/0023222 A1 | 2/2004 | Russell et al. |
| 2004/0166029 A1 | 8/2004 | Losada et al. |
| 2005/0059163 A1 | 3/2005 | Dastane et al. |
| 2006/0054191 A1 | 3/2006 | Higuchi et al. |
| 2006/0131236 A1 | 6/2006 | Belfort et al. |
| 2007/0015191 A1 | 1/2007 | Bitner et al. |
| 2007/0036722 A1 | 2/2007 | Rongved et al. |
| 2007/0075016 A1 | 4/2007 | Leach |
| 2007/0190584 A1 | 8/2007 | Jurgensen et al. |
| 2008/0034509 A1 | 2/2008 | Nuennerich et al. |
| 2009/0042284 A1 | 2/2009 | Tachibana et al. |
| 2010/0285606 A1 | 11/2010 | Phillips et al. |
| 2011/0097816 A1 | 4/2011 | Goodwin |
| 2011/0236884 A1 | 9/2011 | Jablonski et al. |
| 2012/0202225 A1 | 8/2012 | Knutson et al. |
| 2013/0029411 A1 | 1/2013 | Roy et al. |
| 2013/0280767 A1 | 10/2013 | Kobayashi et al. |
| 2014/0161688 A1 | 6/2014 | Campton et al. |
| 2014/0277672 A1 | 9/2014 | Manzarek et al. |
| 2015/0011013 A1 | 1/2015 | Campton et al. |
| 2015/0021963 A1 | 1/2015 | Reed |
| 2015/0219636 A1 | 8/2015 | Rychak et al. |
| 2015/0260178 A1 | 9/2015 | Giessbach |
| 2015/0320924 A1 | 11/2015 | Flieg et al. |
| 2016/0167061 A1 | 6/2016 | McNaughton et al. |
| 2017/0001191 A1 | 1/2017 | Biadillah et al. |
| 2017/0183619 A1 | 6/2017 | Coelho et al. |
| 2018/0171295 A1 | 6/2018 | Shi et al. |
| 2018/0290077 A1* | 10/2018 | McNaughton ..... B01D 21/0084 |
| 2019/0282619 A1* | 9/2019 | Coelho .................. A61K 47/65 |
| 2020/0009614 A1 | 1/2020 | McNaughton et al. |
| 2020/0017830 A1* | 1/2020 | Shi .......................... C12M 47/02 |
| 2020/0072834 A1 | 3/2020 | Busa et al. |
| 2020/0276540 A1 | 9/2020 | Smyslova et al. |
| 2021/0180108 A1 | 6/2021 | Kim et al. |
| 2023/0314428 A1 | 10/2023 | Snow et al. |

FOREIGN PATENT DOCUMENTS

| | | |
|---|---|---|
| EP | 1073716 B1 | 4/2004 |
| EP | 2104488 B1 | 10/2016 |
| GB | 1407267 A | 9/1975 |
| JP | 2001120964 A | 5/2001 |
| JP | 2014521333 A | 8/2014 |
| WO | 2011052927 A2 | 5/2011 |
| WO | 2012090863 A1 | 7/2012 |
| WO | 2013096157 A1 | 6/2013 |
| WO | 2015133972 A1 | 9/2015 |
| WO | 2017109072 A1 | 6/2017 |

(56) References Cited

FOREIGN PATENT DOCUMENTS

| WO | 2017190117 A1 | 11/2017 |
|----|---------------|---------|
| WO | 2023028329 A1 | 3/2023  |

OTHER PUBLICATIONS https://en.wikipedia.org/wiki/Diaphragm_pump (Year: 2021), Document submitted.

https://www.yamadapump.com/what-is-a-double-diaphragm-pump/#:-:text=A (Year: 2021), Document submitted.

Mud Sucker Diaphragm Pumps, https://wastecorp.com/ms-faqs (Year: 2021), Document submitted.

Moon, Sang Ho, "Bio-device for extracting hematopoietic stem cells and mesenchymal stem cells in peripheral blood", Translation of WO 2011/052927 A2, 2011, WIPO, p. 1-23 (Year: 2011).

Wang, Meiyao, "Quantifying CD4 receptor protein in two human CD4+ lymphocyte preparations for quantitative flow cytometry", Clinical proteomics, 11 (1), 43. https://doi.org/10.1186/1559-0275-11-43.

Lloyd, William, et al., "Method and System for Partially or Fully Automated Buoyancy-assisted Separation", U.S. Appl. No. 18/441,894, filed Feb. 14, 2024.

* cited by examiner

Example cell activation and/ or expansion processes

| Example processes in cell & gene therapy process | Timeline |
|---|---|
| • Leukapheresis collection into leukopak bag<br>• Washing of bag to remove excess platelets and red blood cells | Day 1 |
| • Perform a T cell isolation process | Days 1-3 |
| • Activate T cells with buoyant particles<br>• Add genetic material to activated cells through a gene transfer (transfection) process | |
| • Expand / grow engineered cells | Days 3-14 |
| • Formulate and re-inject cells / delivery therapy | Final Day |

FIGURE 7

METHOD AND SYSTEM FOR BUOYANT-PARTICLE-ASSISTED CELL THERAPY

CROSS-REFERENCE TO RELATED APPLICATIONS

This application claims the benefit of U.S. Provisional Application No. 63/326,446, filed 1 Apr. 2022, and U.S. Provisional Application No. 63/434,363, filed 21 Dec. 2022, each of which is incorporated herein in its entirety by this reference.

TECHNICAL FIELD

This invention relates generally to the biological processing fields, and more specifically to a new and useful system and method for buoyant-particle-assisted cell therapy in the biological processing fields.

BACKGROUND

In conventional systems and methods for cell therapy manufacturing, such as those involving magnetic-based separation, a common negative outcome is the overstimulation of cells, such as that which results from cells accumulating in the bottom of a container together with the factors used for stimulation. Other common negative outcomes resulting from conventional cell therapy systems and methods include: an inability to scale (e.g., due to increasing costs of needing larger magnets for larger volumes in magnetic cell separation); low yields; long time periods; and cell death, among others. These outcomes lead to numerous challenges in making cell therapy a widely adoptable and robust process, as the people requiring it are among the sickest and weakest patients, who cannot afford lengthy waits of time or failed procedures.

Thus, there is a need in the biological process field to create an improved and useful system and method for cell therapy manufacturing.

BRIEF DESCRIPTION OF THE FIGURES

FIG. 7 depicts an example set of processes and timeline for buoyant-particle-assisted cell therapy.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

A system for buoyant-particle-assisted cell therapy includes and/or interfaces with a set of buoyant particles. Additionally or alternatively, the system can include and/or interface with a processing container, a set of processing materials (e.g., buffers, factors, solutions, etc.), and/or any other components. Further additionally or alternatively, the system can include and/or interface with any or all of the components as described in any or all of: U.S. application Ser. No. 16/004,874, filed 11 Jun. 2018, U.S. application Ser. No. 14/969,446, filed 15 Dec. 2015, U.S. application Ser. No. 16/506,865, filed 9 Jul. 2019, and U.S. application Ser. No. 17/896,800, filed 26 Aug. 2022, each of which is incorporated in its entirety by this reference.

Figure 1:
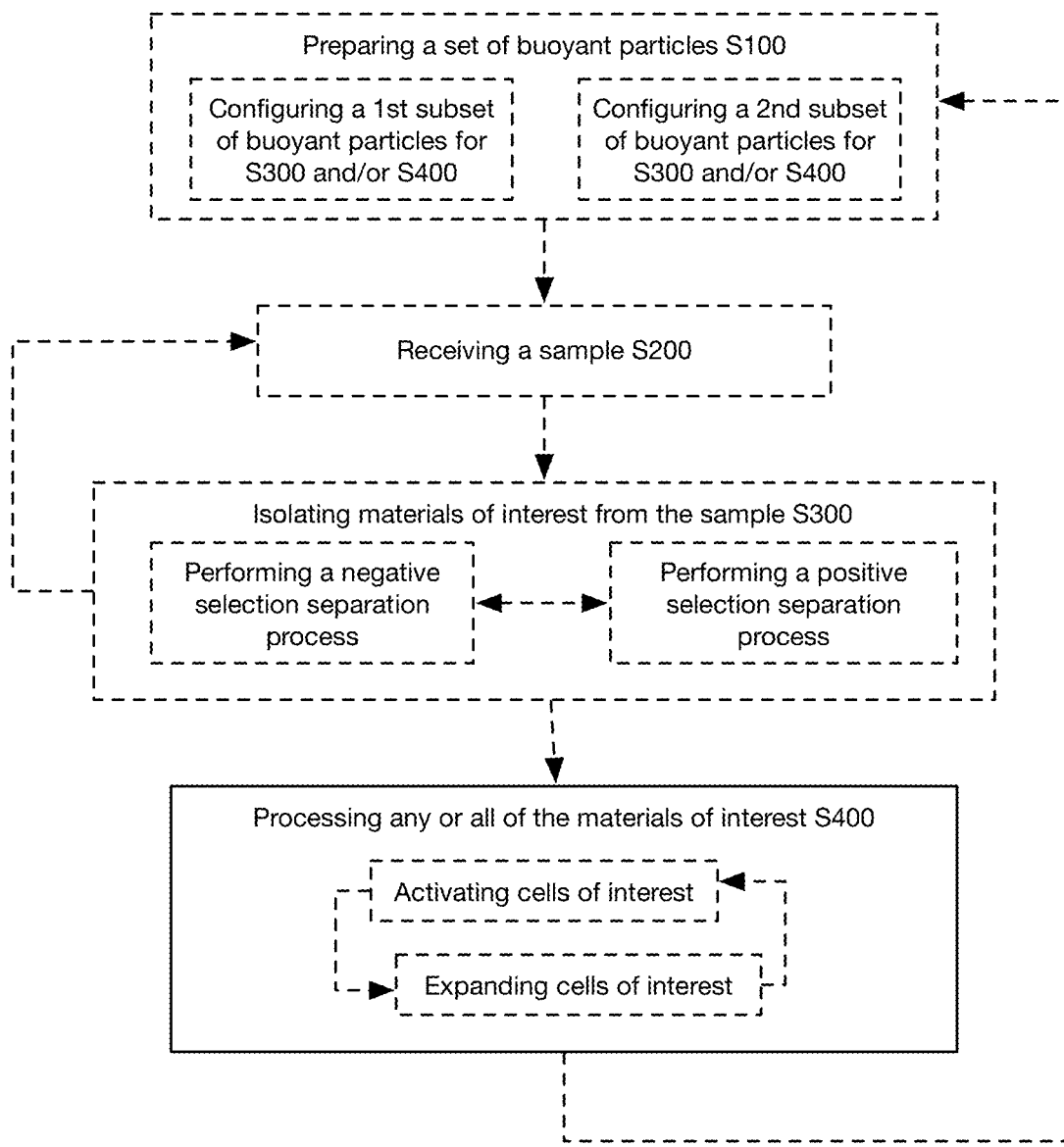
FIG. 1 is a schematic of a method for buoyant-particle-assisted cell therapy.

As shown in FIG. 1, a method 100 for buoyant-particle-assisted cell therapy includes processing the set of cells of interest S400. Additionally or alternatively, the method 100 can include any or all of: preparing a set of buoyant particles S100; receiving a sample S200; and isolating a set of cells of interest from the sample. Further additionally or alternatively, the method U.S. application Ser. No. 16/004,874, filed 11 Jun. 2018, U.S. application Ser. No. 14/969,446, filed 15 Dec. 2015, U.S. application Ser. No. 16/506,865, filed 9 Jul. 2019, and U.S. application Ser. No. 17/896,800, filed 26 Aug. 2022, each of which is incorporated in its entirety by this reference, or any other suitable processes performed in any suitable order. The method 100 can be performed with a system as described above and/or any other suitable system.

2. Benefits

The system and method for buoyant-particle-assisted cell therapy can confer several benefits over current systems and methods.

In a first variation, additional or alternative to those described above, the technology confers the benefit of enabling easy and efficient scaling, such as for significantly larger volumes of biological fluid and/or numbers of cells. In examples, the buoyant cell therapy separation system and/or method is configured for any and/or all volumes of separation, as the separation mechanism is constant, universal, and scalable due to the natural mechanisms (e.g., force of gravity) utilized by the buoyant particles, which cause the buoyant particles to rise with an equal (or near equal) speed through any volume of media or buffer without any special equipment required. This has advantages over magnetic separation systems and methods (among others), as these, for instance, require strong magnetic fields to separate co-stimulatory, particle-bound cells. As such, the larger the reaction system/volume, the larger the magnet that is required, leading to increasing (e.g., exponentially increasing) costs as the system size increases.

In a set of examples, for instance, the system and/or method as implemented with buoyant particle separation enable cell therapy to be performed from volumes at least as small as the wells in cell culture plates (e.g., 48-well plates) to volumes at least as large as those accommodated for in blood bags (e.g., Leukopak bags for T cell isolation processes, 1 or more liters, etc.) without requiring additional equipment, processes, and/or time.

In a second variation, additional or alternative to those described above, the technology confers the benefit of enabling the separation of newly generated cells from any or all of the materials (e.g., buoyant particles, activation factors such as antibodies, etc.) involved in cell activation, which are also present in the solution. In examples, for instance, cells bound to stimulatory microparticles are floating at the surface of the cell culture vessel due to the buoyancy of the microparticles. As the original cells (equivalently referred to herein as parent cells) expand and divide at the surface, the generated cells (e.g., newly-formed cells) (equivalently referred to herein as daughter cells) will detach from the buoyant microparticle-bound cells and sink to the bottom of the container (e.g., due to gravity), whereas the buoyant microparticles with the attached stimulation factors remain floating, allowing for the generation of an untouched population of new cells with spatial separation from the buoyant particles and the co-stimulation factors. This spatial separation contrasts with conventional systems and methods, such as those which are magnetic-based, in which newly-formed cells are in close proximity and/or contact with the co-stimulatory particles, as they both collect at the bottom of the container (e.g., culture well) leading to over-activation (e.g., over-stimulation) of the newly formed cells.

In a set of examples, for instance, the technology confers the benefit of minimizing and/or eliminating the occurrence of overstimulation of the cells. For instance, the generated cells sink to the bottom of the container (e.g., culture and expansion vessel, well plate, centrifuge tube, etc.) and have time to rest (and/or otherwise not be repeatedly activated and/or stimulated) where additional co-stimulation (e.g., re-activation) materials (e.g., buoyant particles bound to activation factors) are not present. This can have numerous advantages over conventional systems and methods, as daughter cells—which are formed directly from the parent cells—initially have many of the same stimulation and/or activation pathways turned on that were active in the parent cell. In specific examples, this is in contrast to conventional iron and/or magnetic-based separation systems (and/or others) in which the cells—including daughter cells—are in constant contact with stimulating particles (e.g., magnetic beads, magnetic beads bound to activation factors, etc.). As soon as the daughter cells separate from the parent cells, they are susceptible to coming into contact (e.g., continuous contact, repeated contact, etc.) with the stimulating particles themselves, which often leads to an overstimulation of cells in a phenomenon known as 'exhaustion'. Once cells reach this state, they typically behave in non-optimal ways (e.g., experience changes in proliferation, rapidly proliferate in a manner that causes the cells to lose biological functions, etc.) for cell therapy applications.

In a third variation, additional or alternative to those described above, the technology confers the benefit of preventing and/or minimizing the occurrence of phagocytosis, which is a common problem with methods using iron particles in which the cells ingest the iron particles. In examples, the system and/or method implement buoyant microparticles that are spatially separated from (e.g., as described above) cells, and/or above a size threshold which can be ingested by cells.

In a fourth variation, additional or alternative to those described above, the technology confers the benefit of increasing a cell yield associated with the cell therapy process. In examples of the system and/or method, a large amount of cells (e.g., compared to conventional methods) are able to be retained during the separation and collection of the cells, as the proliferating cells are easily separable from the buoyant microparticles. This can be in contrast, for instance, to methods involving magnetic iron particles, which often have large populations of cells bound to the magnetic iron particles or cells lost during the separation process, thereby causing the sample which is collected for downstream analysis or other functional assays to have a lower number and/or concentration of cells after separations.

In a fifth variation, additional or alternative to those described above, the technology confers the benefit of reducing the time needed to produce the required therapeutic dose of engineered and/or expanded immune cells (e.g., engineered T cells), such as the minimum amount and/or concentration of produced cells required for entry (e.g., in allogeneic cell therapy) and/or re-entry (e.g., in autologous cell therapy applications) into the user's body. In specific examples, for instance, this time is significantly reduced from the order of weeks (e.g., at least 3 weeks) required for conventional systems and methods, such as to less than a week, within a few days, less than a day, and/or any other times (e.g., as shown in FIG. 7).

In a sixth variation, additional or alternative to those described above, the technology confers the benefit of reducing complications associated with cell therapy processes and/or any other processes involving adherent cells, which have a tendency to stick to the processing container interior (e.g., bottom wall of the processing container).

In a seventh variation, additional or alternative to those described above, the technology confers the benefit of providing a tunable, highly customizable cell therapy manufacturing process through the use of buoyant particles, which is not possible with conventional methodologies. In specific examples, for instance, the use of buoyant particles provides tunability of activation and expansion processes for the cells, where fluid agitation with mixing methods and/or bioreactors can be used to create particle-cell/media supplement interactions at chosen time points and for chosen durations.

Additionally or alternatively, the system and method can confer any other benefit.

3. System

The system preferably functions to perform and/or assist in performing any or all processes associated with cell therapy manufacturing (e.g., activating/stimulating cells, genetically engineering cells, transfecting cells, proliferating [e.g., expanding, replicating, reproducing, etc.] cells, etc.) through the use of buoyant particles. Additionally or alternatively, the system can function to increase and/or optimize any or all of: a yield of cells resulting from the cell therapy manufacturing; an efficiency of any or all of the cell therapy manufacturing; and/or any other parameters. Further additionally or alternatively, the system can be used in conjunction with any other processes (e.g., involving cells, not involving cells, involving other particles, etc.) and/or can perform any other suitable functions.

Cell therapy manufacturing preferably refers herein to any or all of the processes involved in any or all of: the collection of cells (e.g., immune cells, T cells, etc.), modification (e.g., activation, transfection, etc.) of cells, expansion (e.g., proliferation, replication, etc.) of cells, and/or re-introduction of cells (e.g., into the patient) for use in cell therapy applications (e.g., re-introduction of modified immune cells to patients experiencing cancer or other auto-immune conditions). Additionally or alternatively, cell therapy manufacturing can include and/or refer to any or all of the processes of the method, and/or any other suitable processes.

The system for buoyant-particle-assisted cell therapy includes and/or interfaces with a set of buoyant particles (e.g., buoyant spheres, buoyant beads, bubbles, microbubbles, etc.). Additionally or alternatively, the system can include and/or interface with a processing container, a set of processing materials (e.g., buffers, factors, solutions, etc.), and/or any other components. Further additionally or alternatively, the system can include and/or interface with any or all of the components as described in any or all of: U.S. application Ser. No. 16/004,874, filed 11 Jun. 2018, U.S. application Ser. No. 14/969,446, filed 15 Dec. 2015, U.S. application Ser. No. 16/506,865, filed 9 Jul. 2019, and U.S. application Ser. No. 17/896,800, filed 26 Aug. 2022, each of which is incorporated in its entirety by this reference.

Each of the set of buoyant particles is preferably a microbubble (e.g., having a micron-scale diameter, having a diameter less than 1000 microns, having a diameter less than 100 microns, having a diameter between 10 and 100 microns, having a diameter between 40 and 60 microns, etc.), but can additionally include a nanobubble (e.g., having a nanometer-scale diameter, having a diameter less than 1 micron, etc.), and/or any other suitable set of buoyant particles.

The set of buoyant particles (e.g., beads, spheres, micelles, microbubbles) can include any one or more of: glass beads (e.g., silica beads), plastic beads (e.g., polypropylene beads, polyethylene beads, etc.), lipid beads (e.g., stabilized liposome-based beads), hollow beads, solid beads, liquid-filled beads, gas-filled beads, and any other suitable type of particle.

The set of buoyant particles are preferably characterized by a first density lower than that of the density (i.e., a second density) of surrounding fluids (e.g., buffers, solvents, fluids ranging from 0.1 g/cm$^3$ and 0.99 g/cm$^3$, etc.). As such, the buoyant particles are preferably configured to float when placed within the surrounding fluids and/or fluids in a subsequent separation protocol, such as a separation protocol described in U.S. application Ser. No. 16/004,874, filed 11 Jun. 2018, which is incorporated herein in its entirety by this reference. However, buoyant particles can alternatively be configured with any other suitable density relative to that of the other inputs to the system.

In one variation, the set of buoyant particles includes microbubbles (e.g., gas-filled microparticles, hollow microspheres, colloidal bubbles) that can be spheroidal, skirted, ellipsoidal or any other suitable three-dimensional shape. The shape of the microbubbles can vary dynamically in response to the fluid dynamics of surrounding solutions (e.g., changing from one shape to another dictated by gravity, viscosity, and surface tension), but can alternatively be a fixed shape. In a specific example, the microbubbles are composed of borosilicate glass that can include a particle shell surrounding a particle core (e.g., gas filled, fluid-filled, particle-filled, etc.). However, the particle shell can be alternatively composed of any other suitable material including lipids, proteins, surfactants, polymers, and/or any suitable combination thereof. In this example, the glass microbubbles can be fabricated with a fixed spheroidal shape defining a particle diameter (e.g., ranging from between 5 to 30 micron), and a particle shell thickness (e.g., less than 2 microns thick). However, the buoyant particles can be of any other suitable composition, shape, density, and/or dimension.

The set of buoyant particles used in the method 100 preferably include processed (e.g., through surface modifications, functionalized, etc.) buoyant particles, such that the processed buoyant particles are configured to enable/perform one or more processes of the method 100. In preferred variations, for instance, the buoyant particles have undergone one or more surface modifications which configures them for any or all of: binding with activation factors (e.g., as described below), binding with particular cells (e.g., T-cells in a positive selection separation variation of S300, through the binding of the buoyant particles with the activation factors where the activation factors are bound to the cells, etc.); binding with other particles (e.g., particles other than T-cells in a negative selection separation variation of S300); activating (e.g., co-stimulating) cells in S400; and/or configures the buoyant particles for any other processes and/or applications.

In a preferred set of variations, for instance, any or all of the buoyant particles have undergone one or more surface modifications (e.g., in S100), preferably through the application of one or more layers (e.g., chemistries) applied to the buoyant particle surface, wherein the layers include any or all of: molecules, chemicals, moieties, proteins, organic materials, inorganic materials, protective shells, or any other suitable materials. In some variations, for instance, the layers are formed by the solution-based sequential addition of molecules onto the bubble. Additionally or alternatively, surface modifications can be applied by any or all of: in situ polymerization, chemical vapor deposition, polymeric coating in the presence of a solvent, polymeric coating in the absence of a solvent, etching, or otherwise modifying the surface of the input set of buoyant particles.

Each of the surface modifications (e.g., moieties, factors, layers, etc.) preferably functions to facilitate binding with a target material (e.g., cells of interest, other particles, etc.). Additionally or alternatively, any or all of the surface modifications can function to prevent binding, enhance buoyant particle longevity (e.g., shell to prevent breakage), prevent buoyant particle leeching (e.g., shell to prevent leeching on buoyant particle inner contents), and/or perform any other suitable function.

In preferred variations, the processed buoyant particles include buoyant particles functionalized with moieties for binding to a target constituent (e.g., T-cells, red blood cells, white blood cells, circulating tumor cells, stem cells, circulating nucleic acids, etc.) and can include any one or more of: charge-based moieties, nucleic acid-targeting moieties, protein-based moieties (e.g., cell adhesion molecules, growth factors, synthetic proteins), and any other suitable moiety. In a specific example, a particle shell of glass microbubbles can be coated with an aminosilane layer to allow for subsequent surface functionalization with biomolecules (e.g., antibodies, aptamers, lectins, oligos, molecular barcodes, etc.). After glass microbubbles have been aminofunctionalized, the glass microbubbles are preferably crosslinked to streptavidin. However, any other suitable chemical procedure can be performed for surface functionalization of the substrates (e.g., PEGylation, click chemistry, layer-by-layer assembly, ink-jet printing etc.) for selective capture of target constituents, using any other suitable moiety.

Any or all of the other materials involved in the system and/or method can additionally or alternatively be processed, which can function, for instance, to facilitate binding of the materials with the buoyant particles. In a set of preferred variations, for instance, activation factors (e.g., antibodies, CD3 and CD28 antibodies, etc.) are biotinylated through a biotinylation process in which biotin is introduced to (e.g., attaches to) the activation factors, which configures the activation factors to bind with the buoyant particles, such as buoyant particles that have been functionalized with streptavidin. In a set of examples, for instance, biotinylated activation factors (e.g., antibodies) are configured to bind with the cells (e.g., at naturally occurring marker sites of the cells that bind to the activation factors) and to the buoyant factors, which enables the formation of a bound complex, the bound complex including one or more buoyant particles bound to one or more activation factors, where the one or more activation factors are bound to a cell. In the particular specific example shown in FIG. 5, for instance, the microbubbles are configured to bind with one or more CD28 and/or CD3 antibodies (referred to in the key as "Anti-CD28" and "Anti-CD3"), where either or both of these antibody types bind to corresponding marker sites on the cells (e.g., T cells which have marker sites for both of these antibodies). The antibodies can bind in any number to the cells (e.g., limited by the number of marker sites on the cells, limited by the surface area of the cells, etc.) and the buoyant particles can bind in any number to the antibodies (e.g., limited by the number of antibodies bound to a cell, limited by the surface area of the cell and/or the buoyant particle and/or the antibodies).

Additionally or alternatively, the buoyant particles can be configured to bind directly with the cells, the buoyant particles and/or target materials can be otherwise processed or un-processed, and/or the materials can be otherwise suitably configured.

The buoyant particles can additionally and/or alternatively function as a signal delivery agent to target constituents (e.g., via a recombinant molecule bound to the surface of the substrate particle). In a specific example, CD3+ T cells can be captured using functionalized microbubbles targeting CD3 and CD28, proteins that can stimulate the T cell (e.g., inducing cell proliferation and cytokine production), a primary step to manufacturing T cells expressing a chimeric antigen receptor (e.g., CAR-T cells) used in cell therapy (e.g., cancer treatment). However, the substrates can be otherwise configured with any other suitable moiety for multifunctional applications including target-bound complex separation and extraction.

Additionally or alternatively, any or all of the buoyant particles can be unprocessed (e.g., unprocessed, absent of surface modifications, only washed, etc.), partially processed (e.g., glass coated in silane, glass coated in plastic, having a first surface modification, having a subset of surface modifications, polished, etched, etc.), and/or any combination.

The system can optionally additionally or alternatively include and/or interface with any other processing materials, which can include—but are not limited to including—any or all of: chemicals (e.g., functional groups, linkers, etc.), proteins, buffers, reagents, washes, and/or any other suitable materials for maintaining, modifying, or otherwise interacting with the set of buoyant particles.

The system can optionally additionally or alternatively include and/or interface with one or more processing containers (e.g., reaction vessels, processing vessels, tubes, bags, etc.) which function to hold any or all of: the components of the system (e.g., during any or all of the method 100), the particles (e.g., cells, T cells, etc.) being processed, and/or any other materials. In some variants, for instance, the system interfaces with a processing container in the form of a bag or other flexible, high-volume container (e.g., Leukopak bag used in T cell isolation applications, custom expandable bag which is configured to hold and/or segment the bag contents into different sized volumes and/or isolated regions, etc.) Additionally or alternatively, the processing container(s) can be configured for any or all of: capturing any or all of the materials used in the method 100; optimizing any or all of the processes in the method 100; and/or can be otherwise suitably configured. In specific examples, the processing container includes any or all of those described in: U.S. application Ser. No. 16/004,874, filed 11 Jun. 2018, U.S. application Ser. No. 14/969,446, filed 15 Dec. 2015, U.S. application Ser. No. 16/506,865, filed 9 Jul. 2019, and U.S. application Ser. No. 17/896,800, filed 26 Aug. 2022, each of which is incorporated in its entirety by this reference.

In a first set of variations, the system includes a set of buoyant particles, where the set of buoyant particles includes a $1^{st}$ subset of buoyant particles, the $1^{st}$ subset of buoyant particles configured for use in isolating cells of interest in S300, and a $2^{nd}$ subset of buoyant particles configured for use in processing the cells of interest in S400.

The $1^{st}$ and $2^{nd}$ subsets of buoyant particles can be the same, different, or otherwise configured.

In a set of examples, for instance, each of the $1^{st}$ and $2^{nd}$ subsets of buoyant particles are configured to bind with biotinylated factors (e.g., biotinylated antibodies), where the $1^{st}$ subset of buoyant particles are utilized in a negative selection separation process of S300, where in the negative selection separation process, the $1^{st}$ subset of buoyant particles bind to materials (e.g., all other materials) other than the target cells such that the unbound target cells can be collected (e.g., and stored, and frozen, etc.), and the $2^{nd}$ subset of buoyant particles are utilized in a subsequent positive selection separation process of S300, where in the positive selection separation process, the target cells are bound to the buoyant particles (e.g., through the addition of biotinylated antibodies configured to bind with the target cells), which can further initiate processing (e.g., activation, expansion, etc.) of the target cells (e.g., contemporaneously/simultaneously with the positive selection separation process).

In a second set of variations, the system includes a set of buoyant particles which are configured for both S300 and S400.

In a set of examples, for instance, the buoyant particles are configured to bind with a set of activation factors, where the activation factors bind to the target cells, such that the buoyant particles are used to isolate the target cells as well as initiate processing of the target cells (e.g., contemporaneously).

Additionally or alternatively, the buoyant particles can be otherwise suitably configured.

4. Method 100

As shown in FIG. 1, a method 100 for buoyant-particle-assisted cell therapy includes processing any or all materials of interest S400. Additionally or alternatively, the method 100 can include any or all of: preparing a set of buoyant particles S100; receiving a sample S200; and isolating materials of interest from the sample S300. Further additionally or alternatively, the method U.S. application Ser. No. 16/004,874, filed 11 Jun. 2018, U.S. application Ser. No. 14/969,446, filed 15 Dec. 2015, U.S. application Ser. No. 16/506,865, filed 9 Jul. 2019, and U.S. application Ser. No. 17/896,800, filed 26 Aug. 2022, each of which is incorporated in its entirety by this reference, or any other suitable processes performed in any suitable order. The method 100 can be performed with a system as described above and/or any other suitable system.

The method functions to perform, enable, and/or optimize any or all processes involved in cell therapy (e.g., cell therapy manufacturing), and further preferably functions to optimize the production of cells optimized for cell therapy applications (equivalently referred to herein as cell therapy manufacturing), such as through any or all of: increasing a number of cells which are genetically engineered in each cell therapy manufacturing process; decreasing a time which is required for the process to take place; preventing cell death and improving cell efficacy; preventing and/or decreasing the occurrence of overstimulation of the cells; and/or otherwise optimizing a process for cell therapy manufacturing.

The method 100 is preferably configured to be used with immune cells, such as, but not limited to: leukocytes (equivalently referred to herein as white blood cells), (e.g., lymphocytes [e.g., T cells, B cells, etc.], granulocytes [e.g., neutrophils, eosinophils, basophils, etc.], monocytes, etc.), mast cells, macrophages, dendritic cells, natural killer cells, and/or any other immune cells. Additionally or alternatively, the method 100 can be configured for use with non-immune cells, any combination of cells, and/or any other materials (e.g., particles).

In a preferred set of variants, the method 100 is configured for use in T cell therapy applications (e.g., CAR-T cell therapy, CD-19 CAR-T cell therapy, etc.), where the method 100 functions to modify (e.g., activate, stimulate, co-stimulate, etc.) and expand T cells (e.g., to be re-introduced into a patient with an immune condition).

In an additional or alternative set of variations, the method 100 is configured for use in B cell therapy applications.

Additionally or alternatively, the method 100 can be used for and/or interface with any or all of: an autologous cell therapy process, an allogeneic cell therapy process, dendritic cell therapies, therapies involving other immune cells, therapies involving other cells, any other cell therapy process or cell vaccine process, cell culture applications (e.g., outside of cell therapy), non-therapeutic applications (e.g., monocyte culturing), a combination of processes, and/or any other suitable applications.

Alternatively, the method 100 can be used for non-therapeutic applications (e.g., monocyte culturing) and/or any combination of applications.

4.1 Method—Preparing a Set of Buoyant Particles S100

The method 100 can optionally include preparing a set of buoyant particles S100, which functions to configure the set of buoyant particles for any or all of the processes in the method 100. Additionally or alternatively, S100 can function to configure any or all of the set of buoyant particles for optimizing the performance of any or all of the method 100, such as: increasing and/or maximizing a yield of new cells; preventing overstimulation of the cells; and/or optimizing any other processes.

S100 is preferably performed initially in the method 100 and/or prior to any or all of the processes of the method 100 described below, but can additionally or alternatively be performed multiple times during the method 100, and/or at any other times.

Preparing the set of buoyant particles preferably includes processing the set of buoyant particles to bind with desired targets in any or all of the remaining processes of the method 100, such as through any or all of the processing described above. In preferred variations, for instance, a $1^{st}$ subset of a set of buoyant particles are processed (e.g., functionalized) with a first type of surface treatment (e.g., moiety, antibody, etc.) configured to bind with one or more particle types while isolating cells of interest from a remainder of a sample in S300, and a $2^{nd}$ subset of the set of buoyant particles are processed (e.g., functionalized) with a second type of surface treatment (e.g., moiety, factor, antibody, etc.) configured to bind to the cells of interest in another iteration of S300 and/or S400. Additionally or alternatively, the set of buoyant particles can be otherwise suitably processed.

The $1^{st}$ and $2^{nd}$ types of surface treatments can be the same (e.g., cross-linking with streptavidin), different, or any combination of surface treatments.

Additionally or alternatively, all buoyant particles utilized in the method can be configured with the same surface treatment or untreated.

Further additionally or alternatively, any other number of surface treatments can be utilized and applied to all buoyant particles, subsets of buoyant particles, and/or any number of buoyant particles.

S100 can additionally or alternatively include processing any or all of the other materials utilized in the method 100, such as, but not limited to: activation factors, cells, and/or any other materials.

In some variants, for instance, S100 includes adding biotin to any or all of a set of factors configured to bind with any or all of the materials (e.g., factors, antibodies, cells, non-cell materials to be discarded, etc.) configured to bind to the buoyant particles during subsequent processes of the method 100.

Additionally or alternatively, S100 can include any other suitable processes.

4.2 Method—Receiving a Sample S200

The method 100 can optionally include receiving a sample S200, which functions to receive the materials to be processed in subsequent processes of the method 100.

S200 is preferably performed in response to (e.g., after) S100. Additionally or alternatively, iterations of S200 can be performed in response to S300 (e.g., with unbound materials resulting from a negative selection separation process in S300) and/or at any other times. S200 can be performed once or multiple times. Alternatively, the method 100 can be performed in absence of S200.

The sample preferably include cells of interest, and further preferably immune cells (e.g., leukocytes, white blood cells, etc.) which are used in a cell therapy process, such as, but not limited to: lymphocytes (e.g., T cells, B cells, etc.), dendritic cells, and/or any other cells. Alternatively, rather than cells of interest, the method 100 can be configured to process particles other than cells, and/or any other materials.

Additionally or alternatively, the sample can include any other particles, processing materials (e.g., buffers, reagents, etc.), factors (e.g., antibodies), and/or any other materials.

In a set of variations, the sample received in S200 includes the apheresis product resulting from an apheresis process in which a patient with an immune condition provides a blood volume, which is processed through the apheresis process to enrich the patient's white blood cells (e.g., relative to red blood cells) (e.g., forming a Leukopak), thereby increasing a volume of the cells of interest (e.g., T cells) to be processed in further processes of the method 100.

The sample is optionally received at a processing container (e.g., as described above), but can optionally additionally or alternatively be received at any other components and/or locations.

In some variants of the method 100, S200 is performed multiple times. In a set of examples, for instance, a first sample (e.g., received at a first processing container, apheresis product, etc.) is received in a first iteration of S200, the cells of interest isolated from the remaining material of the sample in a first iteration of S300 (e.g., a negative selection separation process), and then the cells of interest are collected from the first processing container to form a second sample (e.g., and located in a second processing container, and remaining in the first processing container, etc.) for use in another iteration of S300 and/or S400.

In other variants, such as those in which the cells of interest are isolated through a positive selection separation process of S300, S200 can be performed once.

Additionally or alternatively, S200 can include any other processes and/or be otherwise suitably performed.

4.3 Method—Isolating Materials of Interest from the Sample S300

The method 100 preferably includes isolating materials of interest from the sample S300, which ultimately functions to isolate the population of cells that are to be processed in S400 (equivalently referred to herein as cells of interest) (e.g., in accordance with a cell therapy manufacturing process). Additionally or alternatively, S300 can function to remove particles and/or portions of the sample from further processing (e.g., in a first iteration of S300), isolate other materials at intermediate iterations of S300, and/or can perform any other functions.

S300 is preferably performed in response to S200, but can additionally or alternatively be performed in response to another process of the method 100, in parallel with (e.g., during) another process of the method 100 (e.g., S400), and/or at any other times. Alternatively, the method 100 can be performed in absence of S300.

The method 100 can include a single iteration of S300, multiple iterations of S300, and/or any number of iterations of S300.

In a preferred set of variations, the cells of interest that are ultimately isolated include T cells and/or a specific subset of T cells (e.g., CD4+ T cells, CD8+ T cells, etc.). Additionally or alternatively, the cells of interest can include any other immune cells (e.g., as described above), any other cells, and/or any combination of cells. Further additionally or alternatively, any other target materials can be isolated in S300.

Figure 2:
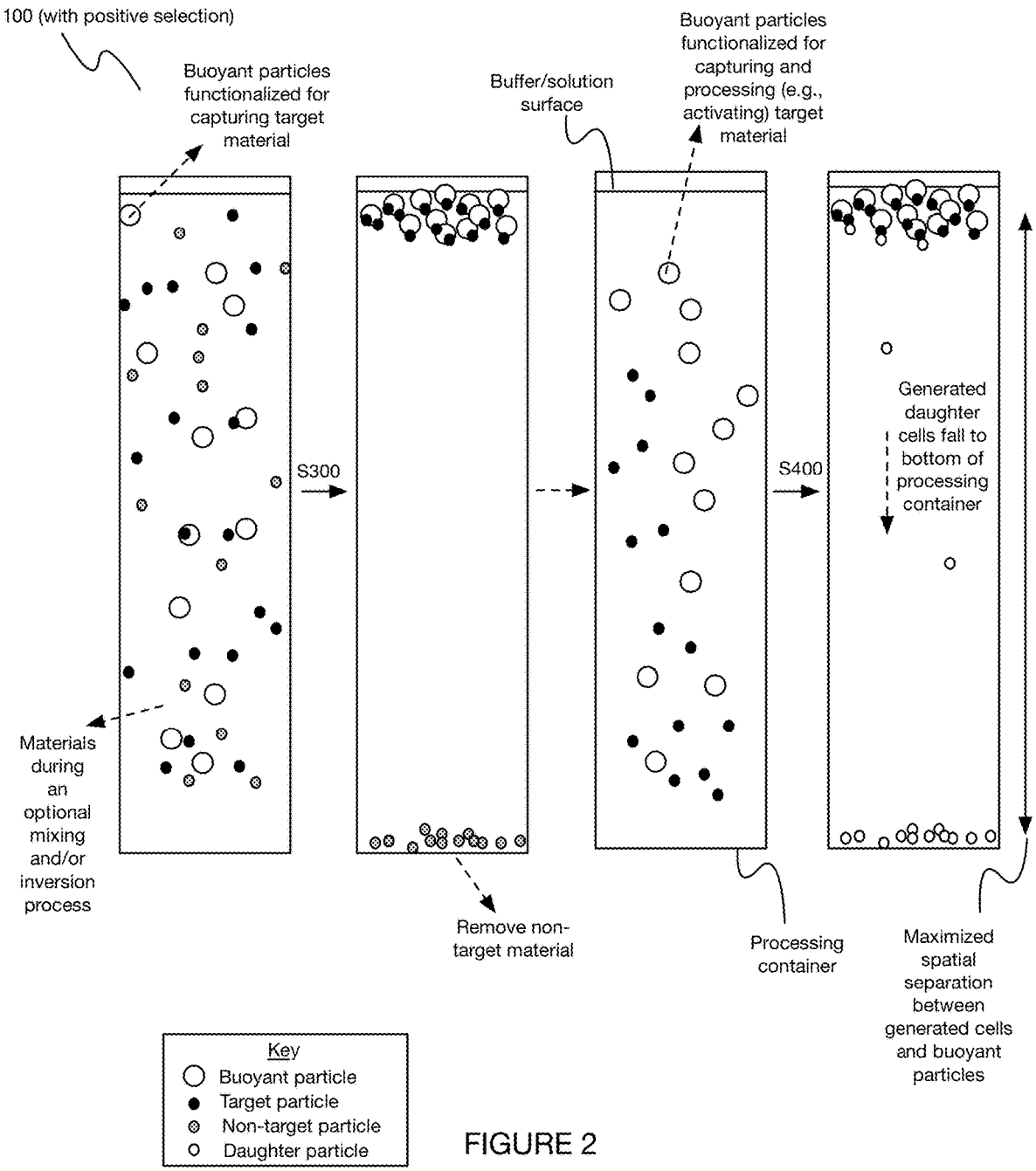
FIG. 2 is a schematic of a variation of the method for buoyant-particle-assisted cell therapy implementing positive selection separation.
Figure 3:
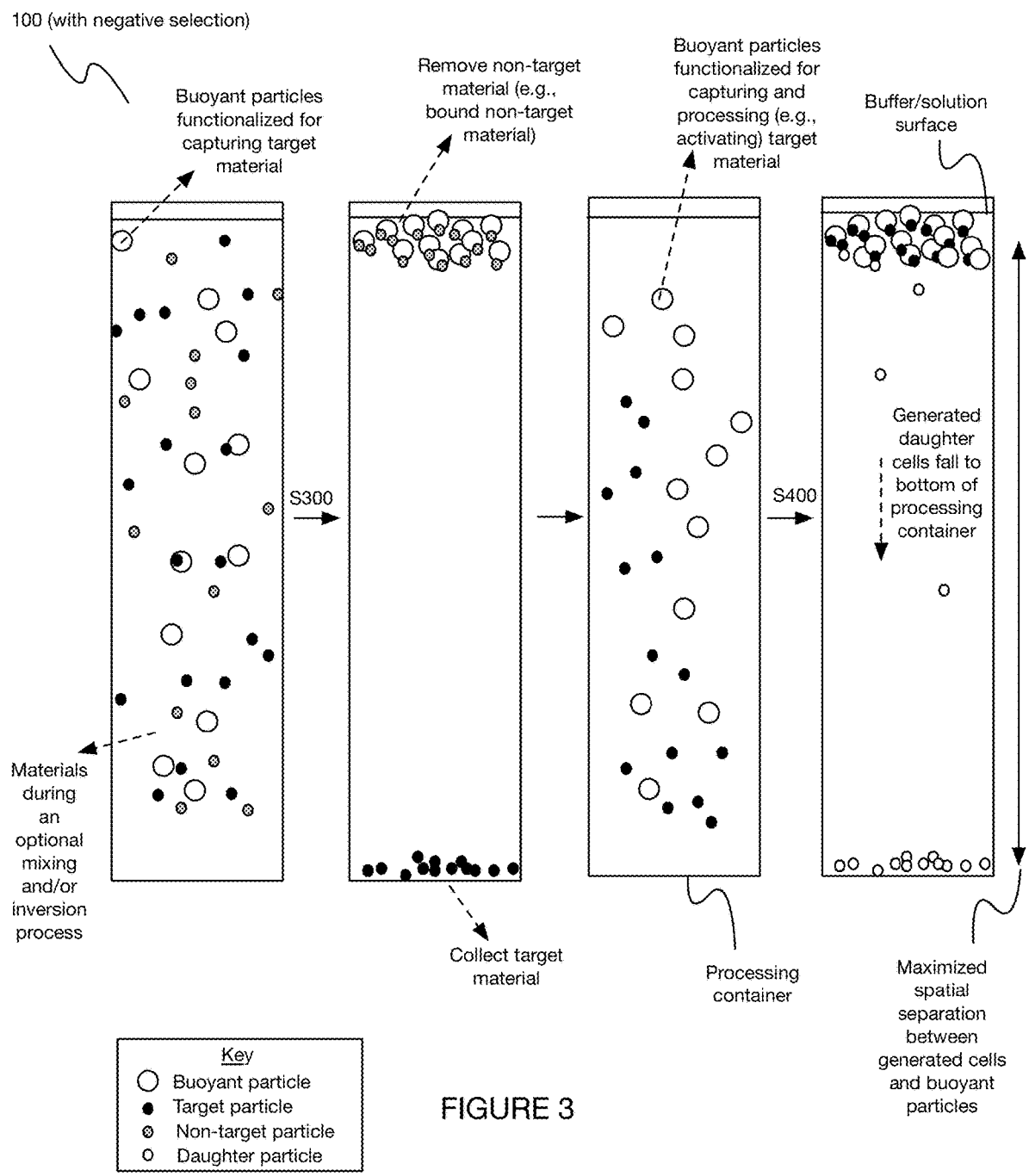
FIG. 3 is a schematic of a variation of the method for buoyant-particle-assisted cell therapy implementing negative selection separation.

S300 is preferably performed with at least one of: a positive selection process (e.g., as shown in FIG. 2), in which buoyant particles are processed and configured (e.g., in S100) to bind with the target material (e.g., cells of interest, cells of interest via factors bound to the cells of interest, etc.); or a negative selection process (e.g., as shown in FIG. 3) in which the buoyant particles are processed and configured (e.g., in S100) to bind with any or all particles other than the target material; either of which functions to enable the target material to be separated from other particles for further processing (e.g., in S400).

In variations of the method including multiple iterations of S300, the multiple iterations can include any or all of: multiple positive selection separation processes, multiple negative selection separation processes, a combination of positive selection and negative selection separation processes, and/or any other processes for isolation of materials of interest.

In variations of the method including a single iteration of S300, S300 preferably includes a positive selection separation process. Alternatively, a single iteration of S300 can include a negative selection separation process and/or be otherwise suitably performed.

In a first set of variants (e.g., as shown in FIG. 2), a set of buoyant particles that each have a surface functionalized to bind directly or indirectly with the target material (e.g., through an antibody-antigen binding of the target cells, via binding of the buoyant particles to a set of activation antibodies bound to the target cells, etc.), wherein the bound target material floats to the surface of the solution and can be isolated (e.g., removed, extracted, etc.) for further processing in S400 (e.g., after removal of the non-target material).

In a first example, a single positive selection process can be implemented to isolate the cells of interest (target cells) (e.g., T cells, other immune cells, etc.) and initiate processing of the cells of interest in S400. In the first example, for instance, a single set of buoyant particles can be used that directly or indirectly bind with the target material, where the optional path from the $2^{nd}$ to the $3^{rd}$ processing container depictions is not implemented in FIG. 2, but rather the bound cells shown in the $2^{nd}$ processing container depiction can be directly used in S400 (e.g., after optionally removing the non-target material, after optionally transferring to a new container, etc.). In this example, the same buoyant particles are effectively used to simultaneously and isolate and process the cells of interest.

In a second example, multiple positive selection processes can be implemented, where a first set of buoyant particles are used to isolate the cells of interest, the isolated cells of interest and then released from the first set of buoyant particles, and then a second set of buoyant particles (e.g., specialized for any or all of the processing in S400) are used to bind to and process the cells of interest. The first and second sets of buoyant particles can be the same, different, or any combination. In this example, all of the processing container depictions shown in FIG. 2 can be implemented.

In another set of variants (e.g., as shown in FIG. 3), the method includes one or more negative selection separation processes in which a set of buoyant particles that have surfaces functionalized to bind with one or more non-target particles are introduced to the sample, wherein the bound non-target material floats to the surface of the solution and can be removed from the sample (or alternatively, the non-target material at the bottom of the container can be extracted) for further processing of the target material. The method further preferably includes a positive selection process to isolate the target materials for further processing. Additionally or alternatively, any combination of separation processes can be used.

In a first example, a first set of buoyant particles are configured (e.g., functionalized) to bind with any or all non-target material in the sample, such that the cells of interest remain unbound. This can be done through any or all of: a single negative selection process, multiple negative selection processes, use of a single type of buoyant particles (e.g., functionalized to bind with factors of the non-target materials and which are not present on the cells of interest, etc.), use of multiple types of buoyant particles (e.g., each subset configured to bind with different types of non-target material), and/or can be performed in any other ways with any suitable materials. Having the cells of interest be unbound after this first separation process can function to enable optimal preservation (e.g., freezing) of the cells of interest for later use (e.g., without having to first release them from buoyant particles). The negative selection separation process(es) can then be followed up with a positive selection process in which the cells of interest are bound to the buoyant particles for processing in S400.

In a particular specific example, the positive selection process can further function to isolate a particular subset of cells of interest, such one or more effector type populations that are optimized for a particular use case (e.g., only CD8+ T cells). Additionally or alternatively, this subset of cells of interest can be isolated from other T cells during a negative selection separation process.

Additionally or alternatively, S300 can include any other processes and/or be performed in any suitable way(s).

4.4 Method—Processing any or all of the Materials of Interest S400

The method 100 preferably includes processing the set of cells of interest S400, which functions to produce (e.g., replicate, manufacture, etc.) cells for cell therapy applications and/or any other use cases. Additionally or alternatively, S400 can function to process other materials, optimize a yield of generated cells, prevent over-activation (e.g., over-stimulation) of the generated cells, and/or perform any other functions.

S400 is preferably performed in response to S300 (e.g., a last iteration of S300, in response to the cells of interest being isolated, in response to the cells of interest being bound to activation factors and buoyant particles, etc.), but can additionally or alternatively be partially or fully performed during S300 (e.g., in parallel with S300), in response to another process, in absence of S300, multiple times during the method 100, and/or at any other suitable time(s).

The materials of interest preferably include the cells of interest isolated in S300, but can additionally or alternatively include any other cells or materials.

Processing the set of cells of interest can include any or all of: promoting and/or enabling the growth and proliferation of the cells of interest; activating (e.g., stimulating, co-stimulating, etc.) the cells of interest; transfecting the cells of interest; expanding (e.g., multiplying, replicating, increasing the amount of, etc.) the cells of interest (e.g., transfected cells of interest); and/or any other processes.

S400 is preferably performed with one or more sets of buoyant particles that are configured for binding with and activating the cells of interest. The one or more sets buoyant particles are preferably the same as those utilized in a positive selection process associated with the cells of interest (e.g., wherein the cells of interest are not separated from the buoyant particles in S300 prior to the performance of S400), but can additionally or alternatively be different than any or all of the buoyant particles used in S300, utilize a combination of types of buoyant particles, and/or be otherwise configured.

Figure 4:
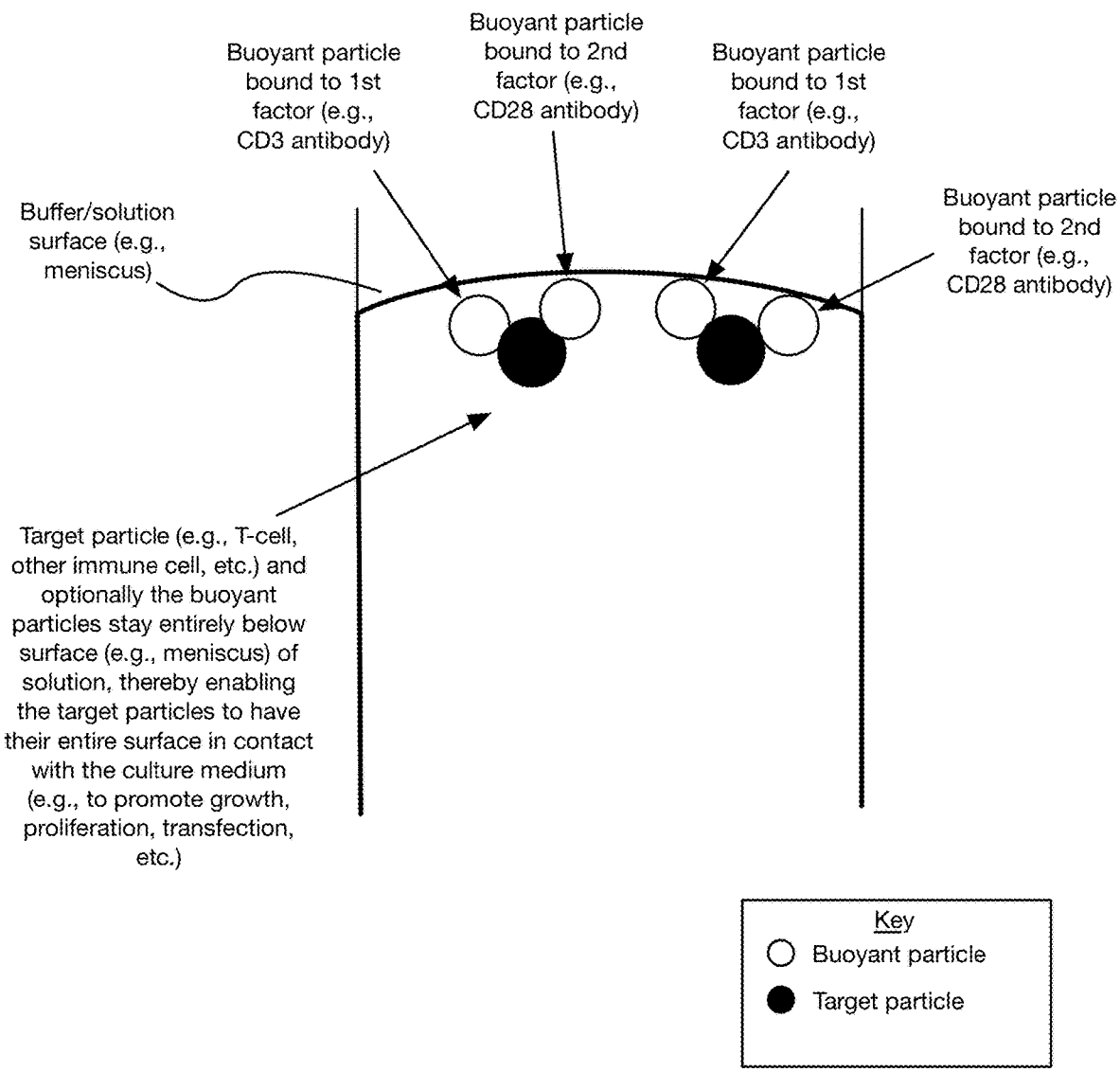
FIG. 4 is a schematic representation of an arrangement of buoyant particles and cells in a processing container.

A potential significant benefit conferred through the use of buoyant particles in S400 is the full or near full contact (e.g., at a whole surface of the cells of interest, at a near whole surface of the cells of interest, etc.) of the cells of interest with the surrounding solution (e.g., buffer, culture medium, etc.) in the processing container. This can enhance any or all of: growth of the cells, proliferation of the cells, transfection of the cells, and/or any other processes. As shown in FIG. 4, for instance, the buoyant particles are submerged below the surface (e.g., meniscus) of the culture medium, enabling a full or maximal surface area of the cells to be in contact with the culture medium.

The use of buoyant particles further preferably benefits to prevent exhaustion (e.g., over-activation and/or repeated activation, over-stimulation and/or repeated stimulation, etc.) of cells (e.g., new cells), as the generated cells fall to the bottom of the processing container (e.g., such that they are not in proximity to the activation factors on the surface of the buoyant particles, such that they cannot be immobilized on the surface of the buoyant particles, etc.), thereby spatially separating and optionally maximizing the distance between the newly generated cells and the buoyant particles and/or activation factors. The floating buoyant particle layer can optionally be associated with and/or form a particular thickness at the top surface (e.g., air/fluid interface), such as, but no limited to: between 1-10 buoyant particles thick, between 10-100 buoyant particles thick, greater than 100 buoyant particles thick, and/or any range between these values and/or intermediate values.

S400 preferably includes and/or enables activating cells (equivalently referred to herein as stimulating cells, etc.). Activating cells preferably functions to initiate the proliferation of cells, thereby increasing the number of cells available (e.g., for further processing, introduction into the patient, etc.). Activating the cells can additionally or alternatively function to enable transfection of the cells (e.g., put a new gene in), such that problematic cells in the body (e.g., cancer cells) cannot evade the transfected cells (e.g., once introduced and/or re-introduced into the user's body), and/or can perform any other functions.

Activating the cells further preferably functions to create a signaling cascade that initiates expansion (e.g., division) of the bound original cells (equivalently referred to herein as parent cells) such that new cells (equivalently referred to herein as daughter cells) are produced. The activation is preferably facilitated and/or optimized through multiple features associated with the binding of the parent cells to the buoyant particles.

Figure 5:
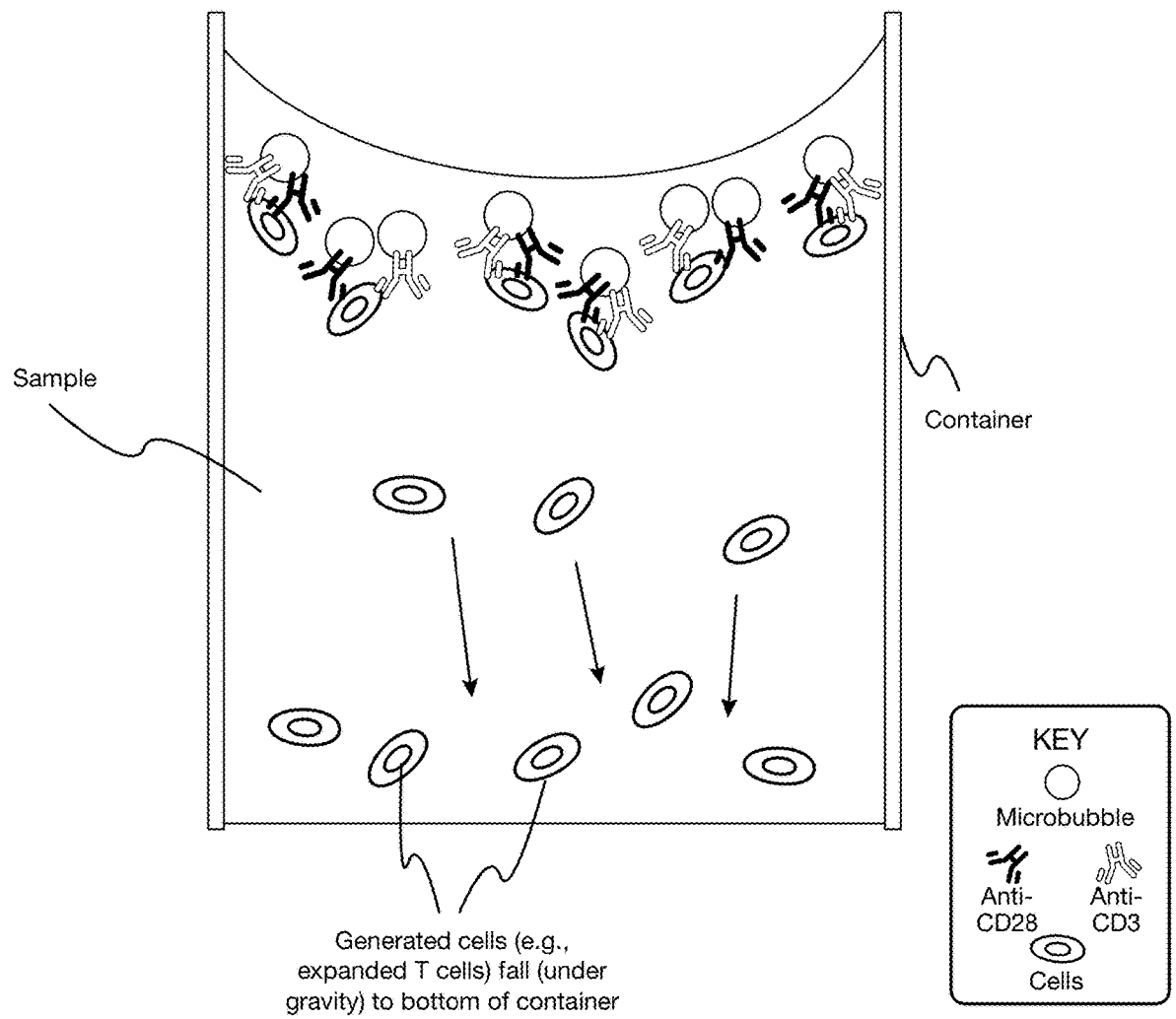
FIG. 5 depicts a variation of a method for buoyant-particle-assisted cell therapy.

First, in preferred variants, activation of the parent cells is at least partially initiated through binding of the parent cells to the activation factors (e.g., antibodies), where the activation factors are specifically selected to initiate activation (e.g., based on the signaling pathways associated with the particular cells of interest). In specific examples involving T cells, for interest, the activation factors include CD3 and CD28 antibodies (e.g., as shown in FIG. 5), which when bound to a T cell (e.g., simultaneously), initiate activation and expansion of the cell. The antibodies, which are preferably added to a sample including the target cells of interest (e.g., in S100, in S200, as described above, etc.) can bind in any number to the target cells of interest.

Second, in preferred variants, activation of the parent cells is enabled and/or optimized through immobilization of the parent cells to the buoyant particles (e.g., through binding of the buoyant particles to the activation factors). This immobilization creates a stronger signaling event (e.g., as compared to non-immobilized cells) and therefore results in stronger activation.

Each parent cell can bind to a single buoyant particle and/or to multiple buoyant particles. Additionally or alternatively, each buoyant particle can bind to multiple parent cells. In preferred variations, such as those involving T cells, the majority (and/or all) of bound cell-buoyant-particle complexes include (e.g., on average) between 1-2 buoyant particles bound to each T cell (e.g., based on particle sizes). Additionally or alternatively, more than 2 buoyant particles can be bound to a cell, multiple cells can be bound to a single buoyant particle, and/or the complexes can be otherwise suitably configured. In example, for instance, any or all of the following can occur: one buoyant particle can be bound to one cell (e.g., through a single antibody site on the cell, through multiple antibody sites on the cell [e.g., through 2 biotinylated antibody types and/or antibody sites on one T cell], etc.); multiple buoyant particles can be bound to a single cell (e.g., through multiple antibody sites on the single cell, through a single antibody site on the single cell, etc.); a single buoyant particle can be bound to multiple cells; and/or any other configurations can occur.

In preferred variations, for instance, an activation process is performed to initiate the proliferation of the cells (e.g., T cells, other lymphocyte cells, other cells, etc.).

In specific examples, the activation process preferably involves a co-stimulation process in which two factors (e.g., CD3 and CD28) (e.g., arranged on different buoyant particles, arranged on the same buoyant particles, etc.) are used to co-stimulate the cells (e.g., T-cells). Additionally or alternatively, the stimulation process can include any other number and/or types of factors.

S400 can additionally or alternatively include expansion (e.g., division) of the parent cells, which functions to produce a large population of cells. Additionally, expansion can function to produce a population of modified cells (e.g., when performed in response to a transduction and/or transfection process). Expansion can be performed at any or all of: in response to a transduction (e.g., transfection), in absence of transduction, in response to activation, simultaneously with activation, and/or at any other suitable times during S400.

In preferred variants, activation (e.g., as described above) causes the parent cells to begin dividing and growing (e.g., according to a certain growth kinetics, according to a certain doubling rate, etc.). The parent cells further preferably divide and grow (e.g., mature) into particularly configured daughter cells, such as effector cells, which can be configured, for instance, to be any or all of: cytotoxic, phagocytic, capable of inducing apoptosis, involved in pro-inflammatory cytokine production, and/or can be otherwise suitably configured. In specific examples involving T cells, for instance, the expanded cells preferably include effector cells of the CD4+ and CD8+ types.

The method 200 can optionally include facilitating the detachment of any or all of the following during culture of the cells: daughter cells from parent cells, parent cells from buoyant particles, and/or any other bound cells. This can function to enable detachment to happen more easily, efficiently, and/or with higher yields. Detachment can occur, for instance, through any or all of the following processes: passive gravity; culturing with agitation (e.g., at the air/water interface); culturing in surfactants such as pluronic to help daughter cells divide off; a spinning process (e.g., which orients the cells so that they are pointed downward, enabling them to fall off more readily; light centrifugation; mixing not involving centrifugation; and/or through any other processes or combination of processes. Additionally or alternatively, the generated cells can fall off naturally (e.g., due to gravity).

Additionally or alternatively, S400 can confer any other benefits and/or include any other suitable processes.

For instance, an additional and/or alternative benefit of using buoyant particles involves facilitating agitation/mixing at the air/water interface during culturing due to the buoyant particle flotation properties. For example, mixing of the buoyant particles (e.g., with buffer, cells, etc.) at this interface (e.g., top layer of buffer in a processing container) can be accomplished with any or all of: sound manipulation, stirring, rocking, and/or any other processes. Further, being in contact with and/or close proximity with air can enhance cell growth, enable the introduction of different gaseous buffers or substances, and/or otherwise confer benefits to the growth and/or proliferation of cells. In a set of specific examples, growth of the cells is facilitated, enhanced, and/or optimized through the cells and their bound buoyant particles being arranged at a gas/buffer interface (e.g., the top surface of the processing container), where diffusion of gas into the fluid occurs more readily, thereby enhancing culturing of the cells (e.g., as compared with culturing occurring at a plastic/buffer interface at the bottom of the processing container in conventional processes with non-buoyant particles).

S400 can optionally additionally or alternatively include transducing (e.g., transfecting) the cells of interest, which is preferably performed after an activation process, but can additionally or alternatively be performed prior to an activation process, during an activation process, during and/or prior to an expansion process, and/or at any other times.

In a preferred set of variants for instance, at some time (e.g., between 1-3 days, less than 1 day, greater than 3 days, etc.) after activation (e.g., while the cells are actively dividing during expansion), the cells are transduced in which the genome of the cell is edited by introducing a new material (e.g., gene, protein, receptor, plasmid, etc.) that gets expressed on/at the cell and can be specifically configured for one or more purposes (e.g., recognizing tumors as foreign).

Additionally or alternatively, transduction can be otherwise suitably performed and/or S400 can be performed in absence of transduction.

S400 can additionally optionally include expanding the cells (e.g., transduced cells) up to a particular and/or predetermined therapeutic dose (e.g., for re-introduction into the patient) and/or volume; removing extraneous materials (e.g., with another iteration of S300) prior to re-introducing the cells back into the patient; and/or any other processes.

S400 can optionally additionally include adding in materials (e.g., factors, cytokines, etc.) to the solution which are configured to promote growth, proliferation, transfection, and/or any other processes associated with the cells of interest.

S400 can optionally additionally include monitoring the cells of interest, such as to detect any or all of: a number and/or growth rate of cells, a level of exhaustion (e.g., to indicate overstimulation) associated with the cells, and/or any other metrics, which can trigger, for instance, an end to S400 (e.g., to introduce the cells into the user's body).

Additionally or alternatively, S400 and/or the method 100 can include any other processes.

5. Variations

In one set of variations (e.g., as shown in FIG. 5), a tube separation container is utilized to isolate T cells using positive selection, wherein the cells are simultaneously activated for transduction and expansion steps. In such variations, the microbubbles are preferably configured to both isolate and activate, which can confer such benefits as improved transduction, expansion, and efficacy because activation occurs in suspension (e.g., away from the bottom of the separation container where the cells are expanding). Additionally or alternatively, this can be performed in any other separation container types (e.g., bag, well plate, etc.).

Figure 6:
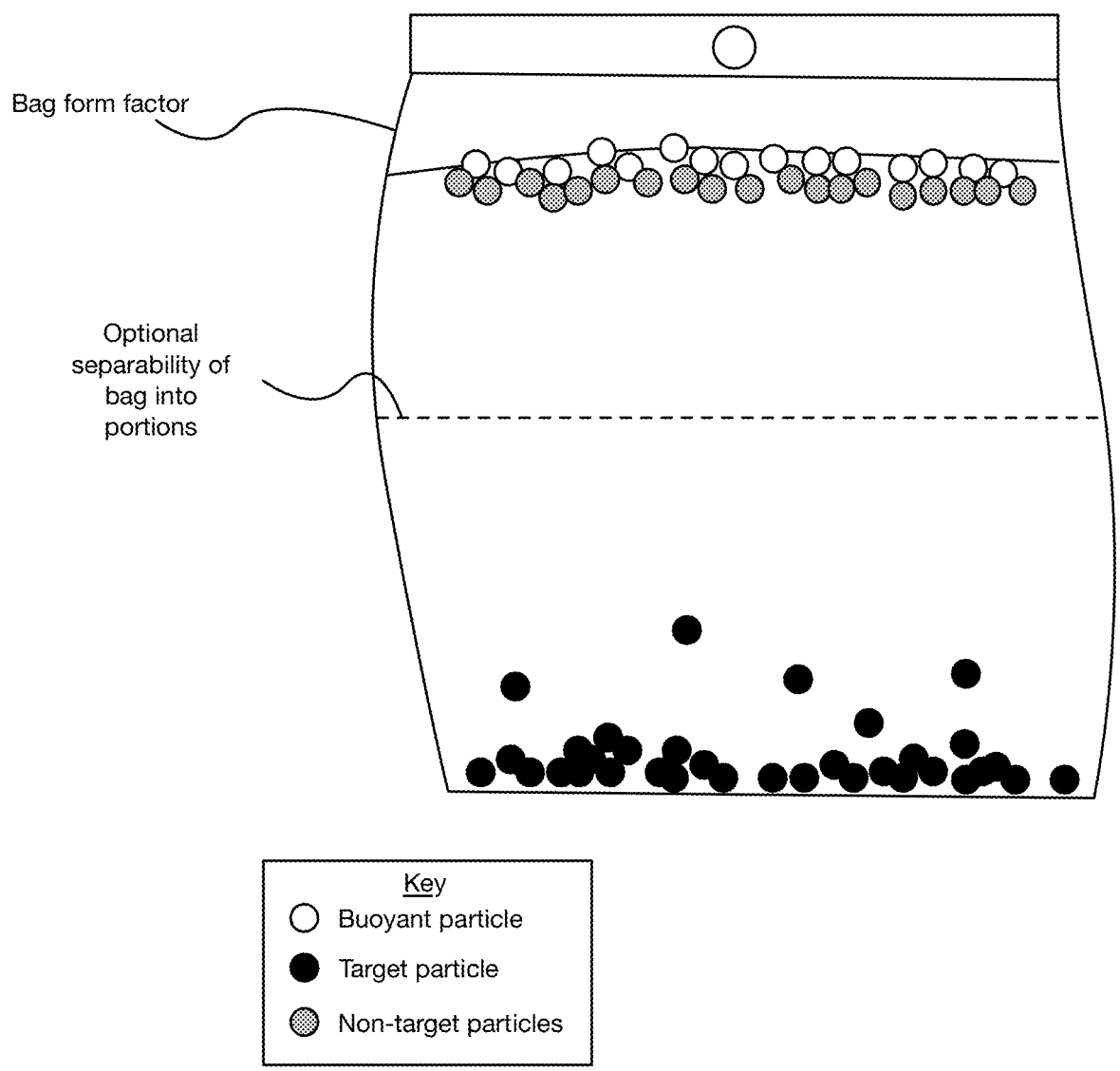
FIG. 6 depicts a variation of a method for buoyant-particle-assisted cell therapy.

In a second set of variations (e.g., as shown in FIG. 6), a bag separation container is implemented (e.g., for T cell isolation using positive selection, for T cell isolation using negative separation, for other types of cell isolation, etc.). The bag separation container can optionally be configured with any number of features, such as features (e.g., sealing mechanisms, barriers, etc.) which enable different regions of the bag (e.g., superior region containing microbubbles and inferior region containing target cells) to be separated (e.g., after one or more steps have been completed) from each other.

In a set of specific examples, any or all of the sample timeline and/or associated steps shown in FIG. 7 can be implemented with a bag (e.g., Leukopak bag) form factor, where the timeline and steps are preferably configured (e.g., individually, collectively, etc.) to improve separation, activation, and expansion (e.g., as enabled through Steps 2 and 3), thereby providing higher yield from isolation and activation to promote optimal cells for faster infusion. Additionally or alternatively, any or all of the timeline and/or steps can be altered, implemented in non-bag embodiments (e.g., tube separation), and/or otherwise suitably implemented.

In a first set of variations of the method, in which the cells of interest have been isolated through a positive selection separation process, the buoyant particles used in S300 can be removed from (e.g., unbound relative to) the cells of interest, and a new set of buoyant particles added in S400, wherein the new set of buoyant particles have surface modifications configured for activation of the cells of interest. In specific examples involving T cells, for instance, the new set of buoyant particles can include a first subset of buoyant particles functionalized with a first factor (e.g., CD3 antibody and/or antigen) and a second subset of buoyant particles functionalized with a second factor (e.g., CD28 antibody and/or antigen). Alternatively, all buoyant particles can be functionalized to bind to either of these antibodies. The set or subsets of buoyant particles are preferably added to the solution and/or cells simultaneously, but can additionally or alternatively be added in series, in partially overlapping times, in non-overlapping times, and/or at any other times. Additionally or alternatively, other cells (e.g., immune cells, non-immune cells, etc.) can be processed, non-cell particles can be processed, a single type (e.g., uniform set) of functionalized buoyant particle (e.g., functionalized for multiple factors) can be used.

Figure 8:
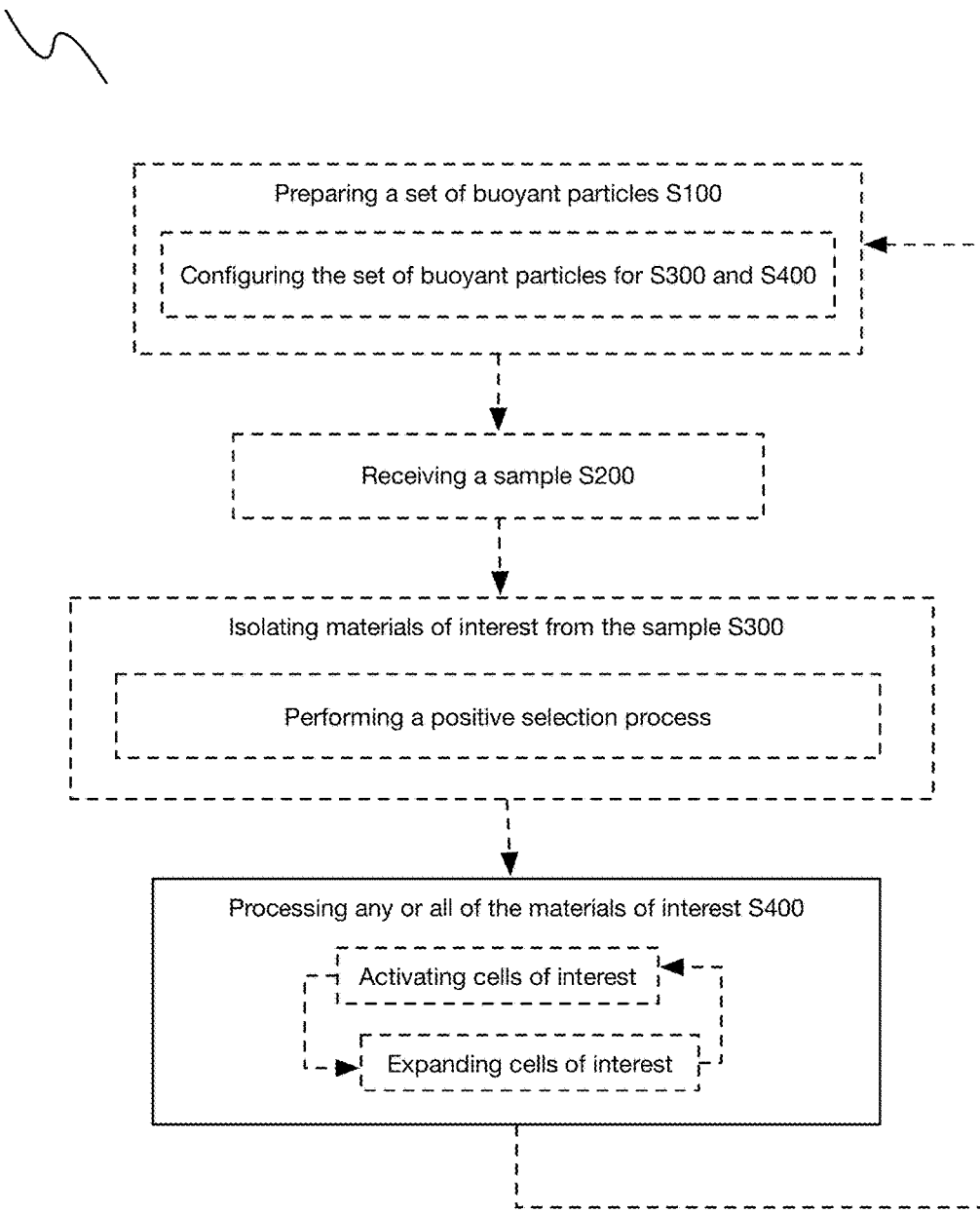
FIG. 8 depicts a variant of the method involving positive selection separation processes.

In a second set of variations of the method (e.g., as shown in FIG. 8), in which the cells of interest have been isolated through a positive selection separation process, the buoyant particles used in S300 can be used in S400. For instance, in examples in which the cells are activated with multiple factors and/or moieties (e.g., CD3 and CD28), the cells can be isolated with buoyant particles having a first factor (or first set of factors) and then interact with a second set of buoyant particles functionalized with a second factor (or second set of factors) in S400 (e.g., wherein an activation process or other process is initiated and/or partially initiated in S300). Additionally or alternatively, the buoyant particles used in the S300 can functionalized with multiple and/or all factors, the buoyant particles used in S300 can include subsets of buoyant particles with different factors, and/or any other buoyant particles can be used.

Figure 9:
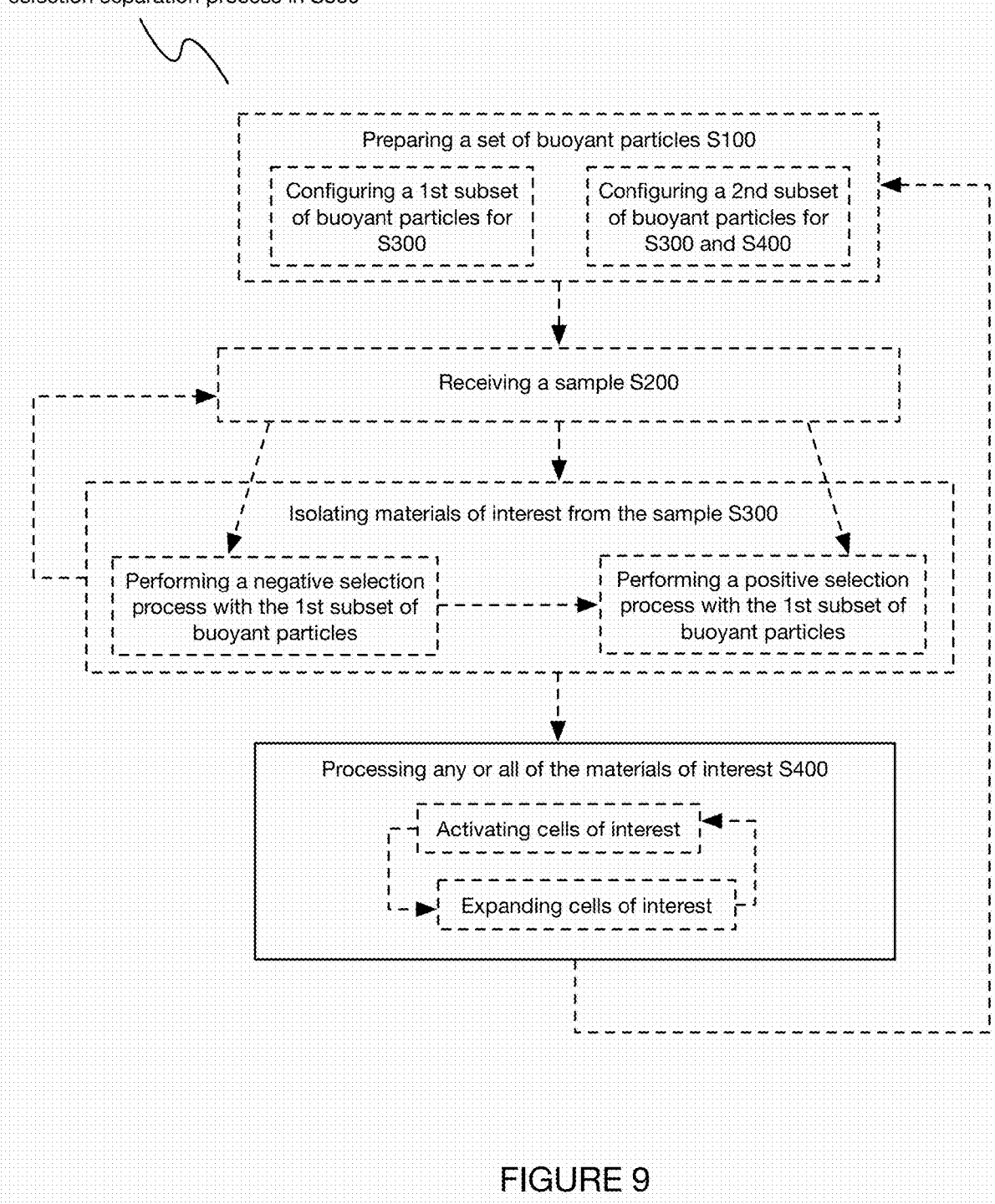
FIG. 9 depicts a variant of the method involving a negative selection separation process.

In a third set of variations of the method, in which the cells of interest have been isolated through a negative selection separation process (e.g., as shown in FIG. 9), the buoyant particles used in S300 are preferably configured to not bind with and/or process (e.g., activate) any of the cells of interest, which can then be cultured and processed (e.g., activated) in S400 with a $1^{st}$ subset of buoyant particles having a $1^{st}$ factor (e.g., CD3 factor) and a $2^{nd}$ subset of buoyant particles having a $2^{nd}$ factor (e.g., CD28 factor). Alternatively, the buoyant particles can be of the same type and configured to bind to multiple factors, and/or the buoyant particles can be otherwise configured.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-public transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-public transitory computer readable media, or any suitable device. The computer-executable component can include a computing system and/or processing system (e.g., including one or more collocated or distributed, remote or local processors) connected to the non-public transitory computer-readable medium, such as CPUs, GPUs, TPUS, microprocessors, or ASICs, but the instructions can alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

We claim:

1. A method for buoyancy-assisted production of cells for a cell therapy, the method comprising:
   initiating a $1^{st}$ selection process, the $1^{st}$ selection process comprising:
     combining T cells and a $1^{st}$ set of buoyant particles, wherein the 1st set of buoyant particles are functionalized with moieties for binding to and forming a complex with the T cells to produce first bound T cells; and
   initiating a cell activation and expansion process comprising a $2^{nd}$ selection process, the cell activation and expansion process comprising:
     producing second bound T cells by combining a set of activators factors, a $2^{nd}$ set of buoyant particles, and the T cells within a container, wherein the set of activation factors are antibodies, wherein the $2^{nd}$ set of buoyant particles are functionalized with moieties for binding to and forming a complex with the antibodies, wherein in at least a portion of the second bound T cells, a single T cell is bound to multiple buoyant particles of the $2^{nd}$ set of buoyant particles, wherein the second bound T cells aggregate at a superior region of the container;
     culturing the second bound T cells in the container to produce daughter cells from the second bound T cells;
     increasing a spatial separation of the daughter cells relative to the second bound T cells, thereby preventing exhaustion of the daughter cells due to exposure of the daughter cells to the antibodies, wherein the daughter cells aggregate at an inferior surface of the container; and
     collecting the daughter cells, wherein the daughter cells are used in the cell therapy.

2. The method of claim 1, wherein the $1^{st}$ and $2^{nd}$ sets of buoyant particles are glass beads.

3. The method of claim 2, wherein each of the $1^{st}$ and $2^{nd}$ sets of buoyant particles comprises streptavidin-functionalized buoyant particles.

4. The method of claim 1, wherein increasing the spatial separation comprises maximizing a distance between the daughter cells and the second bound T cells.

5. The method of claim 1, wherein the second bound T cells comprise multiple ratio values of a number of the antibodies bound to a buoyant particle of the $2^{nd}$ set of buoyant particles.

6. The method of claim 1, wherein in the portion of the second bound T cells in which a single T cell is bound to multiple buoyant particles of the $2^{nd}$ set of buoyant particles, the multiple buoyant particles are submerged within fluid in the container.

7. The method of claim 1, wherein increasing the spatial separation of the daughter cells relative to the second bound T cells comprises agitating the second bound T cells to detach the daughter cells from the second bound T cells.

* * * * *